US012758960B2

(12) United States Patent
Dellamorte et al.

(10) Patent No.: US 12,758,960 B2
(45) Date of Patent: Oct. 13, 2026

(54) PRETREATMENT OF POROUS METAL OXIDE CATALYSTS FOR USE IN DEHYDROGENATION AND OTHER REACTIONS

(71) Applicants: BASF Corporation, Florham Park, NJ (US); THE REGENTS OF THE UNIVERSITY OF CALIFORNIA, Oakland, CA (US)

(72) Inventors: Joseph C. Dellamorte, Wyandotte, MI (US); Carlos Lizandara Pueyo, Fremont, CA (US); Craig Jon Cain-Borgman, Iselin, NJ (US); Enrique Iglesia, Berkeley, CA (US); Junnan Shangguan, Berkeley, CA (US)

(73) Assignee: BASF Corporation, Florham, NJ (US)

( * ) Notice: Subject to any disclaimer, the term of this patent is extended or adjusted under 35 U.S.C. 154(b) by 210 days.

(21) Appl. No.: 18/696,110

(22) PCT Filed: Sep. 26, 2022

(86) PCT No.: PCT/US2022/077002
§ 371 (c)(1),
(2) Date: Mar. 27, 2024

(87) PCT Pub. No.: WO2023/056231
PCT Pub. Date: Apr. 6, 2023

(65) Prior Publication Data

US 2025/0050322 A1 Feb. 13, 2025

Related U.S. Application Data

(60) Provisional application No. 63/261,950, filed on Sep. 30, 2021.

(51) Int. Cl.
*B01J 38/04* (2006.01)
*B01J 23/10* (2006.01)
(Continued)

(52) U.S. Cl.
CPC ............... *B01J 38/04* (2013.01); *B01J 23/10* (2013.01); *B01J 23/92* (2013.01); *B01J 37/031* (2013.01); *C07C 5/322* (2013.01); *C07C 2521/06* (2013.01)

(58) Field of Classification Search
CPC . B01J 21/066; B01J 23/10; B01J 23/92; B01J 37/031; B01J 38/04; B01J 38/50;
(Continued)

(56) References Cited

U.S. PATENT DOCUMENTS 4,999,326 A 3/1991 Sikkenga et al.
5,326,923 A 7/1994 Cooper et al.
(Continued)

FOREIGN PATENT DOCUMENTS

JP S60132652 7/1985
WO 2022/132843 6/2022

OTHER PUBLICATIONS

Concibido et al., "Deactivation and reactivation of Pd/C catalyst used in repeated batch hydrodechlorination of PCE", Applied Catalysis B: Environmental, vol. 11, Issue 1-2, Feb. 8, 2007, pp. 64-69. (Year: 2007).*

(Continued)

*Primary Examiner* — Latosha Hines
(74) *Attorney, Agent, or Firm* — Peter DiMauro

(57) ABSTRACT

Methods of activating and/or reactivating a catalyst composition comprising a porous metal oxide ($MO_x$) catalyst are disclosed. Methods of catalyzing a reaction using a catalyst composition comprising a porous metal oxide catalyst activated and/or reactivated by such a method are also disclosed.

20 Claims, 2 Drawing Sheets

(51) Int. Cl.
*B01J 23/92* (2006.01)
*B01J 37/03* (2006.01)
*C07C 5/32* (2006.01)

(58) Field of Classification Search
CPC ....... B01J 38/52; B01J 38/56; C07C 2521/06; C07C 5/322
See application file for complete search history.

(56) References Cited

U.S. PATENT DOCUMENTS

| | | | | |
|---|---|---|---|---|
| 5,916,835 | A | 6/1999 | Carroll et al. | |
| 2014/0303414 | A1* | 10/2014 | Mazanec | B01J 29/90 502/61 |
| 2018/0036723 | A1 | 2/2018 | Riedel et al. | |

OTHER PUBLICATIONS

Sun et al., Key Roles of Lewis Acid-Base Pairs on ZnxZryOz in Direct Ethanol/Acetone to Isobutene Conversion, Journal of the American Chemical Society, vol. 138, No. 2, Dec. 1, 2015, pp. 507-517. (Year: 2015).

Atanga et al. "Oxidative dehydrogenation of propane to propylene with carbon dioxide", Applied Catalysis B: Environmental 220 (2018) 429-445 Jan. 2018. (Year: 2018).*

International Search Report and Written Opinion of International Application No. PCT/US2022/077002 mailed Dec. 8, 2022, 8 pgs.

Concibido et al., Deactivation and reactivation of Pd/C catalyst used in repeated batch hydrodechlorination of PCE, Applied Catalysis B: Environmental, vol. 11, Issue 1-2, Feb. 8, 2007, pp. 64-69.

Sun et al., Key Roles of Lewis Acid-Base Pairs on ZnxZryOz in Direct Ethanol/Acetone to Isobutene Conversion, Journal of the American Chemical Society, vol. 138, No. 2, Dec. 1, 2015, pp. 507-517.

Zhang et al., Control of coordinatively unsaturated Zr sites in ZrO2 for efficient C-H bond activation, Nature Communications, vol. 9, No. 3794, 2018, pp. 1-10.

European Extended Search Report received in corresponding EP Application No. 22877486.5, mailed Jul. 17, 2025.

Otroshchenko, Tatyana et al.: "ZrO2-based unconventional catalysts for non-oxidative propane dehydrogenation: Factors determining catalytic activity", Journal of Catalysis, Academic Press, Duluth, MN, US, vol. 348, Mar. 20, 2017, pp. 282-290, XP029963542.

Otroshchenko, Tatyana P. et al."Non-oxidative dehydrogenation of propane, n-butane, and, isobutane over bulk ZrO 2-based catalysts: effect of dopant on the active site and pathways of product formation", Catalysis Science & Technology, vol. 7, No. 19, Aug. 30, 2017, pp. 4499-4510, XP055850067.

* cited by examiner

PRETREATMENT OF POROUS METAL OXIDE CATALYSTS FOR USE IN DEHYDROGENATION AND OTHER REACTIONS

This application claims priority to U.S. Provisional Application No. 63/261,950, filed Sep. 30, 2021; the contents which is incorporated herein by reference in its entirety.

Disclosed herein are methods of activating and/or reactivating a catalyst composition comprising a porous metal oxide ($MO_x$) catalyst, e.g., a porous $MO_x$ catalyst whose surface has been rendered at least partially inactive by bound $CO_2$ and/or $H_2O$, e.g., during catalysis or upon exposure to ambient air. Methods of catalyzing a reaction using the catalyst composition activated and/or reactivated by such a method are also disclosed herein.

Dehydrogenation technologies and catalysts have been extensively developed and commercialized in recent years, including, for example, for propane dehydrogenation (PDH). Non-limiting representative PDH technologies include those employing platinum group metal (PGM) catalysts (such as, e.g., Linde-BASF, Oleflex, STAR, and FCDh (DOW) processes), or Cr-containing catalysts (such as, e.g., Catofin and FDB-4 processes). To date, only two Cr- and PGM-free catalyst technologies have been commercially developed: ADHO (China University of Petroleum) and K-PRO (KBR). However, both Cr- and PGM-free catalyst technologies require operation in a fluidized bed reactor and cannot be used in fixed bed reactors.

Metal oxides, such as $ZrO_2$, are a promising alternative for use in a wider range of reactor setups. Illustratively, dehydrogenation of light alkanes has been shown to occur on earth-abundant metal oxides like $ZrO_2$. Specifically, $ZrO_2$ catalysts have been shown to catalyze PDH, exhibiting an initial dehydrogenation activity at 823 K of about 5 mol $kg^{-1}$ $h^{-1}$, which increases to about 11 mol $kg^{-1}$ $h^{-1}$ after 7 hours on stream (40 kPa $C_3H_8$ in $N_2$) in the absence of co-fed $H_2$ (Zhang et al., *Nat. Comm.,* 9:1-10 (2018)).

A major limitation in the use of metal oxides for PDH is their quick deactivation. During the dehydrogenation of hydrocarbons such as propane, the acid-base pairs of metal oxide dehydrogenation catalysts (including $ZrO_2$) may be deactivated due to (i) titrations by $H_2O$ and/or $CO_2$, which directly derive from the gas feed streams or are formed indirectly via reactions of $O_2$ impurities from gas streams with propane and/or $H_2$; and/or (ii) coke deposition resulting from the adsorption of paraffin molecules on M-O sites. In addition, due to the reducibility of some metal oxides, metal oxide dehydrogenation catalysts such as, e.g., $TiO_2$ and $MoO_x$ can be reduced to a lower oxidation state or even the metallic state over time, resulting in deactivation.

Efforts have been made to develop regeneration/reactivation processes for these catalysts. For example, metal oxide catalysts with surfaces rendered at least partially inactive by bound $CO_2$ and/or $H_2O$ may be activated and/or reactivated using high temperature thermal regeneration processes. However, loss of activity due to sintering during the thermal regeneration process is not entirely reversible.

Accordingly, there is a need for alternative regeneration methods for metal oxide catalysts, including methods occurring at lower temperatures than those conventionally used during thermal regeneration treatments.

It has been found that dimethyl ether (DME) may act as a chemical desiccant on $ZrO_2$ surfaces, e.g., by facilitating $H_2O$ removal via a dehydroxylation mechanism as illustrated in FIG. 1. Chemical pretreatment with DME at temperatures below 803 K enables the removal of $H_2O$ and $CO_2$ and the liberation of active sites on zirconia catalysts. Additionally, treatment with methanol (MeOH) may activate metal oxides like $ZrO_2$, potentially due to surface cleaning reactions like those shown in FIG. 2. Moreover, chemical treatment with DME or MeOH is effective for recovering metal oxide catalyst activity after titration using $H_2O$ and $CO_2$ (FIGS. 3, 4).

Thus, surface cleaning reagents such as DME and MeOH may be useful for activating and/or reactivating catalyst compositions comprising metal oxide catalysts, including reactivation at lower temperatures than those conventionally used during thermal regeneration treatments (e.g., >873 K).

Disclosed herein is a method of activating and/or reactivating a catalyst composition comprising a porous metal oxide ($MO_x$) catalyst, the method comprising pretreating the catalyst composition with a surface cleaning reagent, wherein:

- the surface cleaning reagent possesses at least one of the following characteristics:
  - possesses reactivity with one or more bound species derived from $CO_2$ and/or $H_2O$ via a stoichiometric reaction;
  - does not lead to one or more reactions that form a surface titrant of a Lewis acid-base pair; and/or
  - can desorb from a surface of the porous metal oxide catalyst without leaving behind surface debris that can irreversibly titrate an M-O active site of the porous metal oxide catalyst; and further wherein:
- if the porous metal oxide catalyst is $ZrO_2$, then the surface cleaning reagent is not dimethyl ether or propylene.

In some embodiments, if the porous metal oxide catalyst is $ZrO_2$, then the surface cleaning reagent is not methanol.

In some embodiments, the porous metal oxide catalyst has been rendered inactive by bound $H_2O$ and/or $CO_2$. In some embodiments, the porous metal oxide catalyst has been rendered inactive by strongly bound $H_2O$ and/or $CO_2$.

In some embodiments, the porous metal oxide catalyst does not comprise $ZrO_2$.

In some embodiments, the porous metal oxide catalyst comprises at least one of $ZrO_2$, $Y_2O_3$, $CeO_2$, and CoO.

In some embodiments, the porous metal oxide catalyst is chosen from oxides of Y, Ce, and Ti, and mixed oxides thereof.

In some embodiments, the porous metal oxide catalyst comprises one or more of Y, Nb, B. Ga, Co, and Mo on $ZrO_2$.

In some embodiments, the porous metal oxide catalyst comprises one or more of Mg, Ca, Sr, Ba and La on a zirconia support.

In some embodiments, the porous metal oxide catalyst comprises $ZrO_2$-silica, zirconia-alumina, zirconia-titania, or a combination thereof.

In some embodiments, the surface cleaning reagent is chosen from alcohols, ketones, carboxylates, acids, esters, ethers, hemiacetals, hemiketals, acetals, ketals, orthoesters, orthocarbonates, organic acid anhydrides, and combinations thereof.

In some embodiments, the surface cleaning reagent comprises at least one compound chosen from ROH, RCOR', RCHO, ROCOOR', RCOOH, RCOOR', $R_2CH(OR_1)(OH)$, RC(OR")(OH)R', RCH(OR')(OR"), RC(OR")(OR"')R', RC(OR')(OR")(OR"'), C(OR)(OR')(OR")(OR"'), and $R_1(CO)O(CO)R_2$, wherein each of R, R', R", R"', $R_1$, and $R_2$ is independently chosen from alkyl, alkenyl, alkynyl, and aryl groups (e.g., $C_1$-$C_6$ alkyl groups; $C_1$-$C_4$ alkyl groups; $C_6$-$C_{10}$ aryl groups).

In some embodiments, each of R, R', R", R"', $R_1$, and $R_2$ is chosen from methyl, phenyl, and tert-butyl.

In some embodiments, R, R', R", R'", $R_1$, and/or $R_2$ do not possess a —$CH_2CH_3$ group. In some embodiments, R, R', R", R'", $R_1$, and/or $R_2$ do not possess a —$CH_2CH_3$ pendant group. In some embodiments, R, R', R", R'", $R_1$, and/or $R_2$ do not possess a —$CH_2CH_3$ terminal group.

In some embodiments, the surface cleaning reagent is chosen from dimethyl ether, propylene, methanol, anisole, tert-butyl alcohol, methyl tert-butyl ether, di-tert-butyl ether, dimethyl carbonate, and combinations thereof.

In some embodiments, the pretreating is performed at a temperature of up to 900 K. In some embodiments, the pretreating is performed at a temperature of up to 873 K.

In some embodiments, the pretreating is performed for up to 3.6 ks.

In some embodiments, the pretreating is performed at a partial pressure of up to 10 kPa.

In some embodiments, the method further comprises pretreating the catalyst composition in an aerobic oxidative environment before or after the pretreatment with the surface cleaning reagent.

Also disclosed herein is a method of activating and/or reactivating a catalyst composition comprising a porous metal oxide ($MO_x$) catalyst, the method comprising pretreating the catalyst composition with a surface cleaning reagent, wherein:

- the surface cleaning reagent is chosen from alcohols, ketones, carboxylates, acids, esters, ethers, hemiacetals, hemiketals, acetals, ketals, orthoesters, orthocarbonates, organic acid anhydrides, and combinations thereof, and further wherein:
- if the porous metal oxide catalyst is $ZrO_2$, then the surface cleaning reagent is not dimethyl ether or propylene.

In some embodiments, if the porous metal oxide catalyst is $ZrO_2$, then the surface cleaning reagent is not methanol.

In some embodiments, the porous metal oxide catalyst has been rendered inactive by bound $H_2O$ and/or $CO_2$. In some embodiments, the porous metal oxide catalyst has been rendered inactive by strongly bound $H_2O$ and/or $CO_2$.

In some embodiments, the porous metal oxide catalyst does not comprise $ZrO_2$.

In some embodiments, the porous metal oxide catalyst comprises at least one of $ZrO_2$, $Y_2O_3$, $CeO_2$, and CoO.

In some embodiments, the porous metal oxide catalyst is chosen from oxides of Y, Ce, and Ti, and mixed oxides thereof.

In some embodiments, the porous metal oxide catalyst comprises one or more of Y, Nb, B. Ga, Co, and Mo on $ZrO_2$.

In some embodiments, the porous metal oxide catalyst comprises one or more of Mg, Ca, Sr, Ba and La on a zirconia support.

In some embodiments, the porous metal oxide catalyst comprises $ZrO_2$-silica, zirconia-alumina, zirconia-titania, or a combination thereof.

In some embodiments, the surface cleaning reagent is chosen from dimethyl ether, propylene, methanol, anisole, tert-butyl alcohol, methyl tert-butyl ether, di-tert-butyl ether, dimethyl carbonate, and combinations thereof.

In some embodiments, the pretreating is performed at a temperature of up to 900 K. In some embodiments, the pretreating is performed at a temperature of up to 873 K.

In some embodiments, the pretreating is performed for up to 3.6 ks.

In some embodiments, the pretreating is performed at a partial pressure of up to 10 kPa.

In some embodiments, the method further comprises pretreating the catalyst composition in an aerobic oxidative environment before or after the pretreatment with the surface cleaning reagent.

Also disclosed herein is a method of activating and/or reactivating a catalyst composition comprising a porous metal oxide ($MO_x$) catalyst, the method comprising pretreating the catalyst composition with a surface cleaning reagent, wherein:

- the surface cleaning reagent comprises at least one compound chosen from ROH, RCOR', RCHO, ROCOOR', RCOOH, RCOOR', $R_2CH(OR_1)(OH)$, RC(OR")(OH)R', RCH(OR')(OR"), RC(OR")(OR'")R', RC(OR')(O-R")(OR'"), C(OR)(OR')(OR")(OR'"), and $R_1(CO)O(CO)R_2$, wherein each of R, R', R", R'", $R_1$, and $R_2$ is independently chosen from alkyl, alkenyl, alkynyl, and aryl groups (e.g., $C_1$-$C_6$ alkyl groups; $C_1$-$C_4$ alkyl groups; $C_6$-$C_{10}$ aryl groups); and further wherein:
- if the porous metal oxide catalyst is $ZrO_2$, then the surface cleaning reagent is not dimethyl ether or propylene.

In some embodiments, each of R, R', R", R'", $R_1$, and $R_2$ is chosen from methyl, phenyl, and tert-butyl.

In some embodiments, R, R', R", R'", $R_1$, and/or $R_2$ do not possess a —$CH_2CH_3$ group. In some embodiments, R, R', R", R'", $R_1$, and/or $R_2$ do not possess a —$CH_2CH_3$ pendant group. In some embodiments, R, R', R", R'", $R_1$, and/or $R_2$ do not possess a —$CH_2CH_3$ terminal group.

In some embodiments, if the porous metal oxide catalyst is $ZrO_2$, then the surface cleaning reagent is not methanol.

In some embodiments, the porous metal oxide catalyst has been rendered inactive by bound $H_2O$ and/or $CO_2$. In some embodiments, the porous metal oxide catalyst has been rendered inactive by strongly bound $H_2O$ and/or $CO_2$.

In some embodiments, the porous metal oxide catalyst does not comprise $ZrO_2$.

In some embodiments, the porous metal oxide catalyst comprises at least one of $ZrO_2$, $Y_2O_3$, $CeO_2$, and CoO.

In some embodiments, the porous metal oxide catalyst is chosen from oxides of Y, Ce, and Ti, and mixed oxides thereof.

In some embodiments, the porous metal oxide catalyst comprises one or more of Y, Nb, B. Ga, Co, and Mo on $ZrO_2$.

In some embodiments, the porous metal oxide catalyst comprises one or more of Mg, Ca, Sr, Ba and La on a zirconia support.

In some embodiments, the porous metal oxide catalyst comprises $ZrO_2$-silica, zirconia-alumina, zirconia-titania, or a combination thereof.

In some embodiments, the surface cleaning reagent is chosen from dimethyl ether, propylene, methanol, anisole, tert-butyl alcohol, methyl tert-butyl ether, di-tert-butyl ether, dimethyl carbonate, and combinations thereof.

In some embodiments, the pretreating is performed at a temperature of up to 900 K. In some embodiments, the pretreating is performed at a temperature of up to 873 K.

In some embodiments, the pretreating is performed for up to 3.6 ks.

In some embodiments, the pretreating is performed at a partial pressure of up to 10 kPa.

In some embodiments, the method further comprises pretreating the catalyst composition in an aerobic oxidative environment before or after the pretreatment with the surface cleaning reagent.

Also disclosed herein is a method of catalyzing a reaction on a catalyst composition comprising a porous metal oxide catalyst, the method comprising activating and/or reactivating the catalyst composition using a method described herein, wherein the reaction is chosen from alkane dehydrogenation, alkene hydrogenation, olefin-paraffin alkylation, methanol synthesis from $CO/H_2$ mixtures without O-rejection as $H_2O$ or $CO_2$, C—C bond formation via alkene oligomerization or metathesis, dehydrocyclization (alkanes/alkenes to arenes), dehydrocyclodimerization (alkanes/alkenes to arenes with a larger number of C-atoms), transfer hydrogenation, hydroformylation/carbonylation, aromatization, dearomatization, reforming, isomerization, and bifunctional reactions in which one of the aforementioned functions can be combined with a Brønsted acid function.

In some embodiments, the reaction is a reaction described in Table 1A or Table 1B.

TABLE 1A

Summary of the catalytic data of representative propane dehydrogenation reaction technologies

| Technology | FBD-4 | Catofin | Oleflex | PHD |
|---|---|---|---|---|
| Developer | Snamprogetti-Yarsintex | ABB Lummus | UOP | Linde-BASF |
| Time | 1964 | 1986 | 1990 | 1995 |
| Reactor | Fluidized bed | Horizontal fixed bed | Moving bed | Tubular fixed bed |
| Catalyst | $CrO_x/Al_2O_3$ | K(Na)—$CrO_x/Al_2O_3$ | K(Na)Pt—$Sn/Al_2O_3$ | Pt—Sn—$ZrO_2$ |
| T/° C. | 550-600 | 560-650 | 525-705 | 550-650 |
| P/bar | 1.1-1.5 | 0.2-0.5 | 1-3 | >1 |
| WHS/$h^{-1}$ | — | <1 | 4-13 | — |
| Dilute gas | None | None | Cyclic $H_2$ | None |
| Operating period | Continuous regeneration | 15-25 min | Continue operation, 5-10 days | Reaction 6 h, Regeneration 3 h |
| Catalyst life/years | — | 2-3 | 1-3 | >2 |
| Conversion/% | 45-50 | 40-45 | 30-40 | 40-45 |
| Selectivity/% | 80-85 | 82-87 | 85.5-88 | 95 |

TABLE 1B

Summary of the catalytic data of representative propane dehydrogenation reaction technologies

| Technology | STAR | ADHO | FCDh | K-PRO ™ |
|---|---|---|---|---|
| Developer | Phillips | China University of Petroleum | Dow Chemical Company | KBR |
| Time | 1999 | 2016 | 2016 | 2018 |
| Reactor | Tubular fixed bed | Fluidized bed | Up-flow fluidized bed | Fluidized bed (riser) |
| Catalyst | Pt—$Sn/ZnAl_2O_4/CaO$—$Al_2O_3$ | Refractory mixed oxides | Pt—Ga—K/Si—$Al_2O_3$ | Non-Pt, non-Cr |
| T/° C. | 480-620 | 500-650 | ~600 | ~600 |
| P/bar | 5-6 | — | 1 | 1.5 |
| WHS/$h^{-1}$ | 0.5-10 | 1-10 | | |
| Dilute gas | Stream | None | $N_2$ | — |
| Operating period | Reaction 6 h, Regeneration 2 h | Continuous regeneration | Continuous regeneration | Continuous regeneration |
| Catalyst life/years | >5 | — | — | 4-6 |
| Conversion/% | ~35 | ~50 | ~45 | ~45 |
| Selectivity/% | 80-90 | ~90 | ~91 | 87-90 |

In some embodiments, the catalyst composition improves the rate of formation, the yield, or the selectivity of one or more desired products relative to the same reaction performed with the catalyst composition without the activating and/or reactivating.

In some embodiments, the catalyst composition improves product yield at least 2-fold (such as, e.g., 2-fold, at least 5-fold, at least 10-fold, at least 25-fold, at least 50-fold, at least 75-fold, at least 100-fold, at least 125-fold, at least 150-fold, at least 175-fold) compared with a comparable reaction without the activating and/or reactivating.

DEFINITIONS

Figure 1:
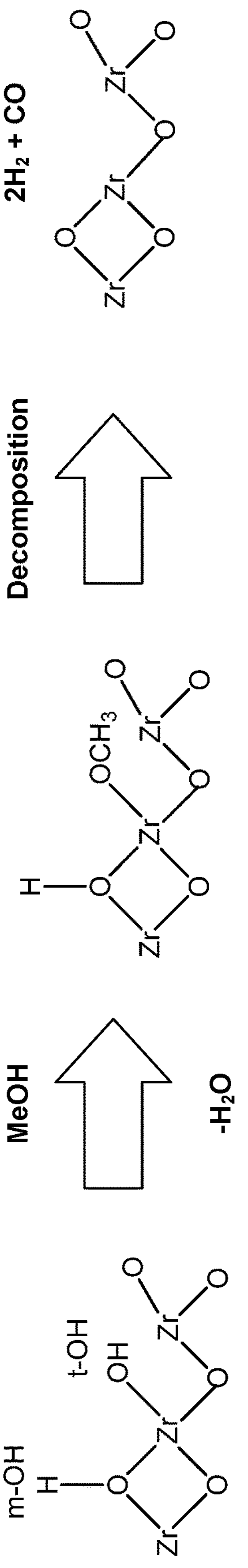
FIG. 1 depicts a dehydroxylation mechanism by which DME may act as a desiccant on a $ZrO_2$ surface.
Figure 2:
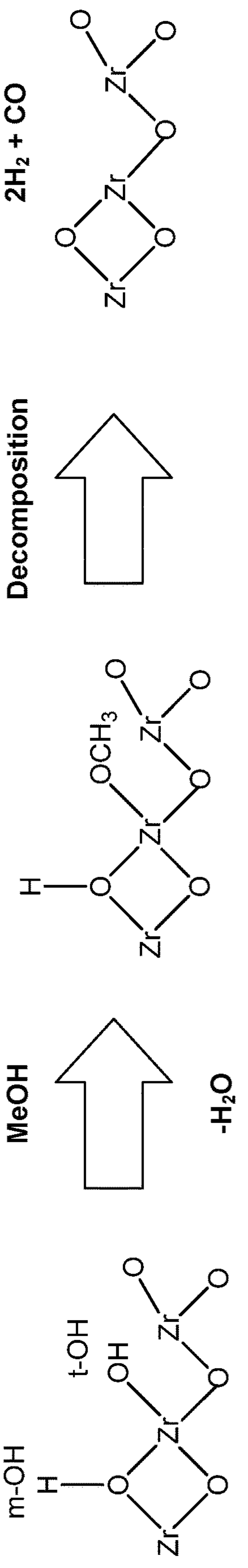
FIG. 2 depicts a mechanism by which MeOH may reactivate a $ZrO_2$ surface.
Figure 3:
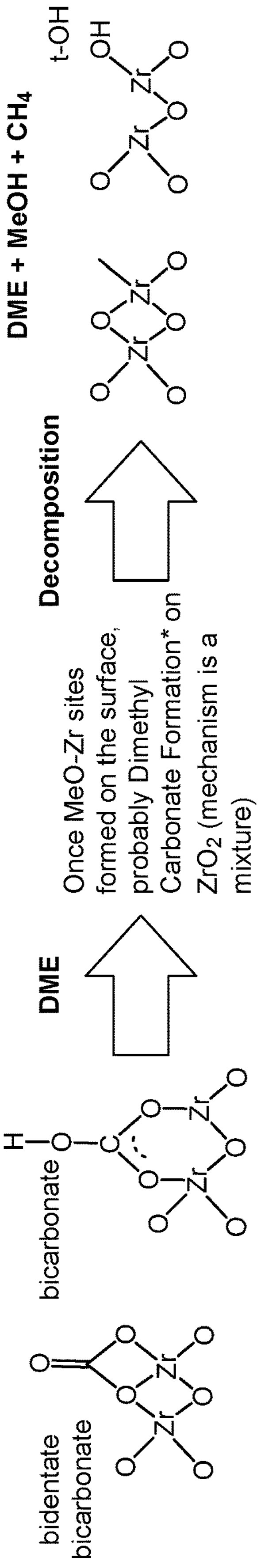
FIG. 3 depicts DME cleaning of a $ZrO_2$ surface via a decarboxylation mechanism.
Figure 4:
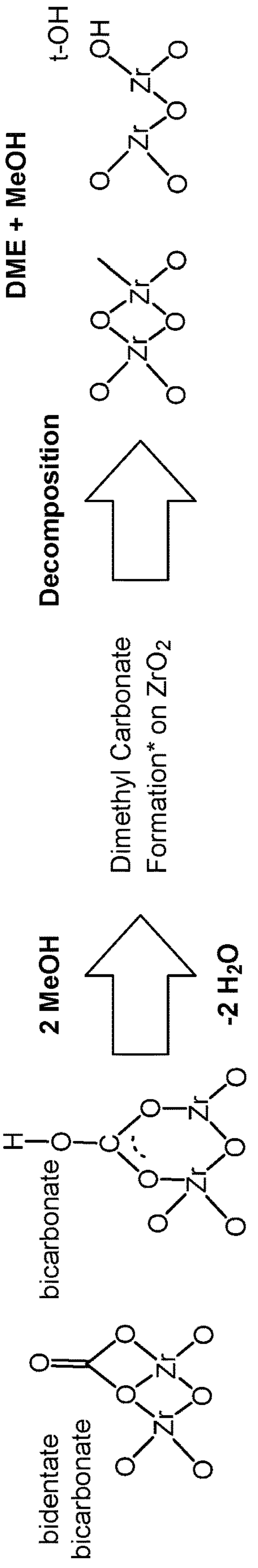
FIG. 4 depicts MeOH cleaning of a $ZrO_2$ surface via a decarboxylation mechanism.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "a" or "an" entity refers to one or more of that entity, e.g., "a compound" refers to one or more compounds or at least one compound unless stated otherwise. As such, the terms "a" (or "an"), "one or more", and "at least one" are used interchangeably herein.

As used herein, the term "and/or" includes any and all combinations of one or more of the associated listed items. Additionally, as used herein, "or" means "and/or."

The term "alkyl," as used herein, refers to a saturated straight-chain (i.e., linear or unbranched) or branched hydrocarbon chain containing carbon atoms (such as, e.g., 1, 2, 3, 4, 5, 6, 7, 8, 9, 10, 11, 12, 13, 14, 15, 16, 17, 18, 19, or 20 carbon atoms). Unless otherwise specified, alkyl groups contain 1-20 carbon atoms. In some embodiments, alkyl groups contain 1-10 carbon atoms (denoted as $C_{1-10}$ alkyl herein). In some embodiments, alkyl groups contain 1-8 carbon atoms (denoted as $C_{1-8}$ alkyl herein). In some embodiments, alkyl groups contain 1-6 carbon atoms (denoted as $C_{1-6}$ alkyl herein). In some embodiments, alkyl groups contain 1-4 carbon atoms (denoted as $C_{1-4}$ alkyl herein). In some embodiments, alkyl groups contain 1-3 carbon atoms (denoted as $C_{1-3}$ alkyl herein). Nonlimiting examples of "alkyl" groups include methyl, ethyl, propyl, isopropyl, isobutyl, tert-butyl, sec-butyl, and the like.

The term "alkenyl," as used herein, means a straight-chain (i.e., linear or unbranched) or branched hydrocarbon chain that contains at least one carbon-carbon double bond. Unless otherwise specified, alkenyl groups contain 2-20 (such as, e.g., 2-12, 2-6, or 2-4) carbon atoms. Nonlimiting examples of "alkenyl" groups include vinyl, allyl, butenyl, pentenyl, hexenyl, butadienyl, pentadienyl, hexadienyl, 2-ethylhexenyl, cyclopent-1-en-1-yl, and the like.

The term "alkynyl," as used herein, means a straight-chain (i.e., linear or unbranched) or branched hydrocarbon chain that contains at least one carbon-carbon triple bond. Unless otherwise specified, alkynyl groups contain 2-20 (such as, e.g., 2-12, 2-6, or 2-4) carbon atoms. Nonlimiting examples of "alkynyl" groups include ethynyl, propynyl, butynyl, pentynyl, hexynyl, and the like.

The term "aryl" refers to monocyclic, bicyclic, and tricyclic ring systems having a total of five to fourteen ring members, wherein at least one ring in the system is aromatic and wherein each ring in the system contains 3 to 7 ring members. The term "aryl," as used herein, also refers to heteroaryl ring systems as defined herein below.

As used herein, the term "catalyst composition" refers to a composition comprising a material that promotes a chemical reaction.

The term "heteroatom," as used herein, refers to an oxygen, sulfur, nitrogen, phosphorus, or silicon (including, any oxidized form of nitrogen, sulfur, phosphorus, or silicon; the quaternized form of any basic nitrogen; or a substitutable nitrogen of a heterocyclic ring, e.g., N (as in 3,4-dihydro-2H-pyrrolyl), NH (as in pyrrolidinyl), or $NR^+$ (as in N-substituted pyrrolidinyl)) atom.

The term "heteroaryl," as used herein, refers to a monocyclic, bicyclic, and tricyclic ring system, including fused or bridged ring systems, having a total of five to fourteen ring members, wherein at least one ring in the system is aromatic, at least one ring in the system contains one or more heteroatoms, and wherein each ring in the system contains 3 to 7 ring members. Non-limiting examples of "heteroaryl" groups include azepinyl, acridinyl, benzimidazolyl, benzothiazolyl, benzindolyl, cinnolinyl, dibenzofuranyl, dibenzothiophenyl, furanyl, isothiazolyl, imidazolyl, indazolyl, indolyl, isoindolyl, indolinyl, isoquinolyl, indolizinyl, isoxazolyl, naphthyridinyl, oxadiazolyl, oxazolyl, pyrrolyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e., thienyl).

As used herein, the term "increase" refers to altering positively, including, but not limited to, altering positively by 1%, altering positively by 5%, altering positively by 10%, altering positively by 25%, altering positively by 30% altering positively by 50%, altering positively by 75%, altering positively by 100%, altering positively by 200%, and the like.

As used herein, the term "decrease" refers to altering negatively, including, but not limited to, altering negatively by 1%, altering negatively by 5%, altering negatively by 10%, altering negatively by 25%, altering negatively by 30%, altering negatively by 50%, altering negatively by 75%, or altering negatively by 100%.

As used herein, the term "pretreating" refers to any process in which a catalyst is contacted with a chemical, combination of chemicals, or a series of chemicals to activate or reactivate the catalyst to a higher activity and/or selectivity state, either before using the catalyst for the intended chemical process or at intervening points in time during use of the catalyst. In some embodiments, pretreating is carried out inside a chemical reactor. In some embodiments, pretreating is carried out outside a chemical reactor. In some embodiments, when used at intervening points during catalyst use, pretreating restores all or a portion of the activity and/or selectivity of the catalyst in protocols that may be denoted to those skilled in the art as catalyst regeneration treatments.

Some embodiments of this disclosure relate to a method of activating and/or reactivating a catalyst composition comprising a porous metal oxide ($MO_x$) catalyst, the method comprising pretreating the catalyst composition with a surface cleaning reagent, wherein:

- the surface cleaning reagent possesses at least one of the following characteristics:
  - possesses reactivity with one or more bound species derived from $CO_2$ and/or $H_2O$ via a stoichiometric reaction;
  - does not lead to one or more reactions that form a surface titrant of a Lewis acid-base pair; and/or
  - can desorb from a surface of the porous metal oxide catalyst without leaving behind surface debris that can irreversibly titrate an M-O active site of the porous metal oxide catalyst; and further wherein:
  - if the porous metal oxide catalyst is $ZrO_2$, then the surface cleaning reagent is not dimethyl ether or propylene.

In some embodiments, if the porous metal oxide catalyst is $ZrO_2$, then the surface cleaning reagent is not methanol.

In some embodiments, the porous metal oxide catalyst has been rendered inactive by bound $H_2O$ and/or $CO_2$. In some embodiments, the porous metal oxide catalyst has been rendered inactive by strongly bound $H_2O$ and/or $CO_2$.

In some embodiments, the surface cleaning reagent possesses reactivity with one or more bound species derived from $CO_2$ and/or $H_2O$ via a stoichiometric reaction.

In some embodiments, the surface cleaning reagent does not lead to one or more reactions that form a surface titrant of a Lewis acid-base pair.

In some embodiments, the surface cleaning reagent can desorb from a surface of the porous metal oxide catalyst without leaving behind surface debris that can irreversibly titrate an M-O active site of the porous metal oxide catalyst.

In some embodiments, the surface cleaning reagent possesses reactivity with one or more bound species derived from $CO_2$ and/or $H_2O$ via a stoichiometric reaction; and the surface cleaning reagent does not lead to one or more reactions that form a surface titrant of a Lewis acid-base pair.

In some embodiments, the surface cleaning reagent possesses reactivity with one or more bound species derived from $CO_2$ and/or $H_2O$ via a stoichiometric reaction; and the surface cleaning reagent can desorb from a surface of the porous metal oxide catalyst without leaving behind surface debris that can irreversibly titrate an M-O active site of the porous metal oxide catalyst.

In some embodiments, the surface cleaning reagent does not lead to one or more reactions that form a surface titrant of a Lewis acid-base pair; and the surface cleaning reagent can desorb from a surface of the porous metal oxide catalyst without leaving behind surface debris that can irreversibly titrate an M-O active site of the porous metal oxide catalyst.

In some embodiments, the surface cleaning reagent possesses all of the following characteristics:

possesses reactivity with one or more bound species derived from $CO_2$ and/or $H_2O$ via a stoichiometric reaction;

does not lead to one or more reactions that form a surface titrant of a Lewis acid-base pair; and/or can desorb from a surface of the porous metal oxide catalyst without leaving behind surface debris that can irreversibly titrate an M-O active site of the porous metal oxide catalyst.

In some embodiments, the surface cleaning reagent is chosen from alcohols, ketones, carboxylates, acids, esters, ethers, hemiacetals, hemiketals, acetals, ketals, orthoesters, orthocarbonates, organic acid anhydrides, and combinations thereof.

In some embodiments, the surface cleaning reagent comprises at least one compound chosen from ROH, RCOR', RCHO, ROCOOR', RCOOH, RCOOR', $R_2CH(OR_1)(OH)$, RC(OR")(OH)R', RCH(OR')(OR"), RC(OR")(OR"')R', RC(OR')(OR")(OR"'), C(OR)(OR')(OR")(OR"'), and $R_1(CO)O(CO)R_2$, wherein each of R, R', R", R"', $R_1$, and $R_2$ is independently chosen from alkyl, alkenyl, alkynyl, and aryl groups (e.g., $C_1$-$C_6$ alkyl groups; $C_1$-$C_4$ alkyl groups; $C_6$-$C_{10}$ aryl groups).

In some embodiments, each of R, R', R", R"', $R_1$, and $R_2$ is chosen from methyl, phenyl, and tert-butyl.

In some embodiments, R, R', R", R"', $R_1$, and/or $R_2$ do not possess a —$CH_2CH_3$ group. In some embodiments, R, R', R", R"', $R_1$, and/or $R_2$ do not possess a —$CH_2CH_3$ pendant group. In some embodiments, R, R', R", R"', $R_1$, and/or $R_2$ do not possess a —$CH_2CH_3$ terminal group.

In some embodiments, the surface cleaning reagent is chosen from dimethyl ether, propylene, methanol, anisole, tert-butyl alcohol, methyl tert-butyl ether, di-tert-butyl ether, dimethyl carbonate, and combinations thereof.

In some embodiments, the surface cleaning reagent is chosen from dimethyl ether, propylene, and methanol.

In some embodiments, the surface cleaning reagent is dimethyl ether.

In some embodiments, the surface cleaning reagent is propylene.

In some embodiments, the surface cleaning reagent is methanol.

In some embodiments, the porous metal oxide catalyst possesses a surface with an M-O site of the Lewis type and of balanced acid-base strength.

In some embodiments, a surface of the porous metal oxide catalyst stabilizes anionic and/or cationic moieties that form at transition states for heterolytic processes that form and cleave C—H bonds.

In some embodiments, a metal (M) of the porous metal oxide catalyst does not undergo reduction to a lower oxidation state in a reductive environment typical of hydrogenation-dehydrogenation catalysis.

In some embodiments, the porous metal oxide catalyst possesses a surface with an M-O site of the Lewis type and of balanced acid-base strength; a surface of the porous metal oxide catalyst stabilizes anionic and/or cationic moieties that form at transition states for heterolytic processes that form and cleave C—H bonds; and a metal (M) of the porous metal oxide catalyst does not undergo reduction to a lower oxidation state in a reductive environment typical of hydrogenation-dehydrogenation catalysis.

In some embodiments, the porous metal oxide catalyst is chosen from oxides of Y, Ce, and Ti, and mixed oxides thereof.

In some embodiments, the porous metal oxide catalyst comprises one or more of Y, Nb, B. Ga, Co, and Mo on $ZrO_2$.

In some embodiments, the porous metal oxide catalyst comprises one or more of Mg, Ca, Sr, Ba and La on a zirconia support.

In some embodiments, the porous metal oxide catalyst comprises $ZrO_2$-silica, zirconia-alumina, zirconia-titania, or a combination thereof.

In some embodiments, the porous metal oxide catalyst comprises at least one of $ZrO_2$, $Y_2O_3$, $CeO_2$, and CoO. In some embodiments, the porous metal oxide catalyst comprises more than one of $ZrO_2$, $Y_2O_3$, $CeO_2$, and CoO.

In some embodiments, the porous metal oxide catalyst comprises $ZrO_2$. In some embodiments, the porous metal oxide catalyst is $ZrO_2$.

In some embodiments, the porous metal oxide catalyst comprises Y-stabilized $ZrO_2$. In some embodiments, the porous metal oxide catalyst is Y-stabilized $ZrO_2$.

In some embodiments, the porous metal oxide catalyst comprises $Y_2O_3$. In some embodiments, the porous metal oxide catalyst is $Y_2O_3$.

In some embodiments, the pretreating is performed at a temperature of up to 900 K. In some embodiments, the pretreating is performed at a temperature of up to 873 K. In some embodiments, the pretreating is performed at a temperature of up to 823 K. In some embodiments, the pretreating is performed at a temperature of up to 723 K.

In some embodiments, the pretreating is performed at a temperature between 323 K and 900 K. In some embodiments, the pretreating is performed at a temperature between 323 K and 873 K. In some embodiments, the pretreating is performed at a temperature between 323 K and 823 K. In some embodiments, the pretreating is performed at a temperature between 323 K and 723 K.

In some embodiments, the method further comprises pretreating the catalyst composition in an aerobic oxidative environment before or after the pretreatment with the surface cleaning reagent.

In some embodiments, the method further comprises pretreating the catalyst composition in an aerobic oxidative environment before the pretreatment with the surface cleaning reagent.

In some embodiments, the method further comprises pretreating the catalyst composition in an aerobic oxidative environment after the pretreatment with the surface cleaning reagent.

Some embodiments of this disclosure relate to a method of activating and/or reactivating a catalyst composition comprising a porous metal oxide ($MO_x$) catalyst, the method comprising pretreating the catalyst composition with a surface cleaning reagent, wherein:

the surface cleaning reagent is chosen from alcohols, ketones, carboxylates, acids, esters, ethers, hemiacetals, hemiketals, acetals, ketals, orthoesters, orthocarbonates, organic acid anhydrides, and combinations thereof, and further wherein:

if the porous metal oxide catalyst is $ZrO_2$, then the surface cleaning reagent is not dimethyl ether or propylene.

In some embodiments, if the porous metal oxide catalyst is $ZrO_2$, then the surface cleaning reagent is not methanol.

In some embodiments, the porous metal oxide catalyst has been rendered inactive by bound $H_2O$ and/or $CO_2$. In some embodiments, the porous metal oxide catalyst has been rendered inactive by strongly bound $H_2O$ and/or $CO_2$.

In some embodiments, the surface cleaning reagent possesses reactivity with one or more bound species derived from $CO_2$ and/or $H_2O$ via a stoichiometric reaction.

In some embodiments, the surface cleaning reagent does not lead to one or more reactions that form a surface titrant of a Lewis acid-base pair.

In some embodiments, the surface cleaning reagent can desorb from a surface of the porous metal oxide catalyst without leaving behind surface debris that can irreversibly titrate an M-O active site of the porous metal oxide catalyst.

In some embodiments, the surface cleaning reagent possesses reactivity with one or more bound species derived from $CO_2$ and/or $H_2O$ via a stoichiometric reaction; and the surface cleaning reagent does not lead to one or more reactions that form a surface titrant of a Lewis acid-base pair.

In some embodiments, the surface cleaning reagent possesses reactivity with one or more bound species derived from $CO_2$ and/or $H_2O$ via a stoichiometric reaction; and the surface cleaning reagent can desorb from a surface of the porous metal oxide catalyst without leaving behind surface debris that can irreversibly titrate an M-O active site of the porous metal oxide catalyst.

In some embodiments, the surface cleaning reagent does not lead to one or more reactions that form a surface titrant of a Lewis acid-base pair; and the surface cleaning reagent can desorb from a surface of the porous metal oxide catalyst without leaving behind surface debris that can irreversibly titrate an M-O active site of the porous metal oxide catalyst.

In some embodiments, the surface cleaning reagent is chosen from dimethyl ether, propylene, methanol, anisole, tert-butyl alcohol, methyl tert-butyl ether, di-tert-butyl ether, dimethyl carbonate, and combinations thereof.

In some embodiments, the surface cleaning reagent is chosen from dimethyl ether, propylene, and methanol.

In some embodiments, the surface cleaning reagent is dimethyl ether.

In some embodiments, the surface cleaning reagent is propylene.

In some embodiments, the surface cleaning reagent is methanol.

In some embodiments, the porous metal oxide catalyst possesses a surface with an M-O site of the Lewis type and of balanced acid-base strength.

In some embodiments, a surface of the porous metal oxide catalyst stabilizes anionic and/or cationic moieties that form at transition states for heterolytic processes that form and cleave C—H bonds.

In some embodiments, a metal (M) of the porous metal oxide catalyst does not undergo reduction to a lower oxidation state in a reductive environment typical of hydrogenation-dehydrogenation catalysis.

In some embodiments, the porous metal oxide catalyst possesses a surface with an M-O site of the Lewis type and of balanced acid-base strength; a surface of the porous metal oxide catalyst stabilizes anionic and/or cationic moieties that form at transition states for heterolytic processes that form and cleave C—H bonds; and a metal (M) of the porous metal oxide catalyst does not undergo reduction to a lower oxidation state in a reductive environment typical of hydrogenation-dehydrogenation catalysis.

In some embodiments, the porous metal oxide catalyst is chosen from oxides of Y, Ce, and Ti, and mixed oxides thereof.

In some embodiments, the porous metal oxide catalyst comprises one or more of Y, Nb, B. Ga, Co, and Mo on $ZrO_2$.

In some embodiments, the porous metal oxide catalyst comprises one or more of Mg, Ca, Sr, Ba and La on a zirconia support.

In some embodiments, the porous metal oxide catalyst comprises $ZrO_2$-silica, zirconia-alumina, zirconia-titania, or a combination thereof.

In some embodiments, the porous metal oxide catalyst comprises at least one of $ZrO_2$, $Y_2O_3$, $CeO_2$, and CoO. In some embodiments, the porous metal oxide catalyst comprises more than one of $ZrO_2$, $Y_2O_3$, $CeO_2$, and CoO.

In some embodiments, the porous metal oxide catalyst comprises $ZrO_2$. In some embodiments, the porous metal oxide catalyst is $ZrO_2$.

In some embodiments, the porous metal oxide catalyst comprises Y-stabilized $ZrO_2$. In some embodiments, the porous metal oxide catalyst is Y-stabilized $ZrO_2$.

In some embodiments, the porous metal oxide catalyst comprises $Y_2O_3$. In some embodiments, the porous metal oxide catalyst is $Y_2O_3$.

In some embodiments, the pretreating is performed at a temperature of up to 900 K. In some embodiments, the pretreating is performed at a temperature of up to 873 K. In some embodiments, the pretreating is performed at a temperature of up to 823 K. In some embodiments, the pretreating is performed at a temperature of up to 723 K.

In some embodiments, the pretreating is performed at a temperature between 323 K and 900 K. In some embodiments, the pretreating is performed at a temperature between 323 K and 873 K. In some embodiments, the pretreating is performed at a temperature between 323 K and 823 K. In some embodiments, the pretreating is performed at a temperature between 323 K and 723 K.

In some embodiments, the method further comprises pretreating the catalyst composition in an aerobic oxidative environment before or after the pretreatment with the surface cleaning reagent.

In some embodiments, the method further comprises pretreating the catalyst composition in an aerobic oxidative environment before the pretreatment with the surface cleaning reagent.

In some embodiments, the method further comprises pretreating the catalyst composition in an aerobic oxidative environment after the pretreatment with the surface cleaning reagent.

Some embodiments of this disclosure relate to a method of activating and/or reactivating a catalyst composition comprising a porous metal oxide ($MO_x$) catalyst, the method comprising pretreating the catalyst composition with a surface cleaning reagent, wherein:

the surface cleaning reagent comprises at least one compound chosen from ROH, RCOR', RCHO, ROCOOR', RCOOH, RCOOR', $R_2CH(OR_1)(OH)$, RC(OR")(OH)R', RCH(OR')(OR"), RC(OR")(OR''')R', RC(OR')(OR")(OR'''), C(OR)(OR')(OR")(OR'''), and $R_1(CO)O(CO)R_2$, wherein each of R, R', R", R''', $R_1$, and $R_2$ is independently chosen from alkyl, alkenyl, alkynyl, and aryl groups (e.g., $C_1$-$C_6$ alkyl groups; $C_1$-$C_4$ alkyl groups; $C_6$-$C_{10}$ aryl groups); and further wherein:

if the porous metal oxide catalyst is $ZrO_2$, then the surface cleaning reagent is not dimethyl ether or propylene.

In some embodiments, if the porous metal oxide catalyst is $ZrO_2$, then the surface cleaning reagent is not methanol.

In some embodiments, the porous metal oxide catalyst has been rendered inactive by bound $H_2O$ and/or $CO_2$. In some embodiments, the porous metal oxide catalyst has been rendered inactive by strongly bound $H_2O$ and/or $CO_2$.

In some embodiments, each of R, R', R'', R''', $R_1$, and $R_2$ is chosen from methyl, phenyl, and tert-butyl.

In some embodiments, R, R', R'', R''', $R_1$, and/or $R_2$ do not possess a —$CH_2CH_3$ group. In some embodiments, R, R', R'', R''', $R_1$, and/or $R_2$ do not possess a —$CH_2CH_3$ pendant group. In some embodiments, R, R', R'', R''', $R_1$, and/or $R_2$ do not possess a —$CH_2CH_3$ terminal group.

In some embodiments, the surface cleaning reagent possesses reactivity with one or more bound species derived from $CO_2$ and/or $H_2O$ via a stoichiometric reaction.

In some embodiments, the surface cleaning reagent does not lead to one or more reactions that form a surface titrant of a Lewis acid-base pair.

In some embodiments, the surface cleaning reagent can desorb from a surface of the porous metal oxide catalyst without leaving behind surface debris that can irreversibly titrate an M-O active site of the porous metal oxide catalyst.

In some embodiments, the surface cleaning reagent possesses reactivity with one or more bound species derived from $CO_2$ and/or $H_2O$ via a stoichiometric reaction; and the surface cleaning reagent does not lead to one or more reactions that form a surface titrant of a Lewis acid-base pair.

In some embodiments, the surface cleaning reagent possesses reactivity with one or more bound species derived from $CO_2$ and/or $H_2O$ via a stoichiometric reaction; and the surface cleaning reagent can desorb from a surface of the porous metal oxide catalyst without leaving behind surface debris that can irreversibly titrate an M-O active site of the porous metal oxide catalyst.

In some embodiments, the surface cleaning reagent does not lead to one or more reactions that form a surface titrant of a Lewis acid-base pair; and the surface cleaning reagent can desorb from a surface of the porous metal oxide catalyst without leaving behind surface debris that can irreversibly titrate an M-O active site of the porous metal oxide catalyst.

In some embodiments, the surface cleaning reagent is chosen from dimethyl ether, propylene, methanol, anisole, tert-butyl alcohol, methyl tert-butyl ether, di-tert-butyl ether, dimethyl carbonate, and combinations thereof.

In some embodiments, the surface cleaning reagent is chosen from dimethyl ether, propylene, and methanol.

In some embodiments, the surface cleaning reagent is dimethyl ether.

In some embodiments, the surface cleaning reagent is propylene.

In some embodiments, the surface cleaning reagent is methanol.

In some embodiments, the porous metal oxide catalyst possesses a surface with an M-O site of the Lewis type and of balanced acid-base strength.

In some embodiments, a surface of the porous metal oxide catalyst stabilizes anionic and/or cationic moieties that form at transition states for heterolytic processes that form and cleave C—H bonds.

In some embodiments, a metal (M) of the porous metal oxide catalyst does not undergo reduction to a lower oxidation state in a reductive environment typical of hydrogenation-dehydrogenation catalysis.

In some embodiments, the porous metal oxide catalyst possesses a surface with an M-O site of the Lewis type and of balanced acid-base strength; a surface of the porous metal oxide catalyst stabilizes anionic and/or cationic moieties that form at transition states for heterolytic processes that form and cleave C—H bonds; and a metal (M) of the porous metal oxide catalyst does not undergo reduction to a lower oxidation state in a reductive environment typical of hydrogenation-dehydrogenation catalysis.

In some embodiments, the porous metal oxide catalyst is chosen from oxides of Y, Ce, and Ti, and mixed oxides thereof.

In some embodiments, the porous metal oxide catalyst comprises one or more of Y, Nb, B. Ga, Co, and Mo on $ZrO_2$.

In some embodiments, the porous metal oxide catalyst comprises one or more of Mg, Ca, Sr, Ba and La on a zirconia support.

In some embodiments, the porous metal oxide catalyst comprises $ZrO_2$-silica, zirconia-alumina, zirconia-titania, or a combination thereof.

In some embodiments, the porous metal oxide catalyst comprises at least one of $ZrO_2$, $Y_2O_3$, $CeO_2$, and CoO. In some embodiments, the porous metal oxide catalyst comprises more than one of $ZrO_2$, $Y_2O_3$, $CeO_2$, and CoO.

In some embodiments, the porous metal oxide catalyst comprises $ZrO_2$. In some embodiments, the porous metal oxide catalyst is $ZrO_2$.

In some embodiments, the porous metal oxide catalyst comprises Y-stabilized $ZrO_2$. In some embodiments, the porous metal oxide catalyst is Y-stabilized $ZrO_2$.

In some embodiments, the porous metal oxide catalyst comprises $Y_2O_3$. In some embodiments, the porous metal oxide catalyst is $Y_2O_3$.

In some embodiments, the pretreating is performed at a temperature of up to 900 K. In some embodiments, the pretreating is performed at a temperature of up to 873 K. In some embodiments, the pretreating is performed at a temperature of up to 823 K. In some embodiments, the pretreating is performed at a temperature of up to 723 K.

In some embodiments, the pretreating is performed at a temperature between 323 K and 900 K. In some embodiments, the pretreating is performed at a temperature between 323 K and 873 K. In some embodiments, the pretreating is performed at a temperature between 323 K and 823 K. In some embodiments, the pretreating is performed at a temperature between 323 K and 723 K.

In some embodiments, the method further comprises pretreating the catalyst composition in an aerobic oxidative environment before or after the pretreatment with the surface cleaning reagent.

In some embodiments, the method further comprises pretreating the catalyst composition in an aerobic oxidative environment before the pretreatment with the surface cleaning reagent.

In some embodiments, the method further comprises pretreating the catalyst composition in an aerobic oxidative environment after the pretreatment with the surface cleaning reagent.

Some embodiments of this disclosure relate to a method of catalyzing a reaction on a catalyst composition comprising a porous metal oxide catalyst, the method comprising activating and/or reactivating the catalyst composition using a method described herein, wherein the reaction is chosen from alkane dehydrogenation, alkene hydrogenation, olefin-paraffin alkylation, methanol synthesis from $CO/H_2$ mixtures without O-rejection as $H_2O$ or $CO_2$, C—C bond formation via alkene oligomerization or metathesis, dehydrocyclization (alkanes/alkenes to arenes), dehydrocyclodimerization (alkanes/alkenes to arenes with a larger number of C-atoms), transfer hydrogenation, hydroformylation/carbonylation, aromatization, dearomatization, reforming, isomerization, and bifunctional reactions in which one of the aforementioned functions can be combined with a Brønsted acid function.

In some embodiments, the method further comprises activating and/or reactivating using a method described herein more than once.

In some embodiments, the bifunctional reaction is chosen from catalytic reforming for octane enhancement, alkane hydroisomerization, and hydrocracking.

In some embodiments, the bifunctional reaction is chosen from isodewaxing, hydrocracking, fluid catalytic cracking, and reactions converting $C_3$-$C_4$ alkanes to aromatics.

In some embodiments, the reaction is alkane dehydrogenation. In some embodiments, the method further comprises cycling between actively dehydrogenating the light alkane gas or light alkene gas with the catalyst composition and reactivating the catalyst composition. In some embodiments, the method further comprises cycling between actively dehydrogenating the light alkane gas or light alkene gas with the catalyst composition and reactivating the catalyst composition. In some embodiments, the method is performed using a plurality of reactors in which the reaction and the activating and/or reactivating are performed alternately.

In some embodiments, the reaction is propane dehydrogenation.

In some embodiments, the reaction occurs in a reactor. In some embodiments, the reactor is chosen from U-shape quartz reactors, packed tubular reactors, fluidized bed reactors, circulating fluidized bed reactors, fixed bed reactors, cycled fixed bed reactors, multi-tubular reactors, cycled sets of multi-tubular reactors and a moving bed reactor, and reactor systems comprising combinations thereof.

In some embodiments, the porous metal oxide catalyst possesses a surface with an M-O site of the Lewis type and of balanced acid-base strength.

In some embodiments, a surface of the porous metal oxide catalyst stabilizes anionic and/or cationic moieties that form at transition states for heterolytic processes that form and cleave C—H bonds.

In some embodiments, a metal (M) of the porous metal oxide catalyst does not undergo reduction to a lower oxidation state in a reductive environment typical of hydrogenation-dehydrogenation catalysis.

In some embodiments, the porous metal oxide catalyst possesses a surface with an M-O site of the Lewis type and of balanced acid-base strength; a surface of the porous metal oxide catalyst stabilizes anionic and/or cationic moieties that form at transition states for heterolytic processes that form and cleave C—H bonds; and a metal (M) of the porous metal oxide catalyst does not undergo reduction to a lower oxidation state in a reductive environment typical of hydrogenation-dehydrogenation catalysis.

In some embodiments, the porous metal oxide catalyst comprises at least one of $ZrO_2$, $Y_2O_3$, $CeO_2$, and CoO. In some embodiments, the porous metal oxide catalyst comprises more than one of $ZrO_2$, $Y_2O_3$, $CeO_2$, and CoO.

In some embodiments, the porous metal oxide catalyst comprises $ZrO_2$. In some embodiments, the porous metal oxide catalyst is $ZrO_2$.

In some embodiments, the porous metal oxide catalyst comprises Y-stabilized $ZrO_2$. In some embodiments, the porous metal oxide catalyst is Y-stabilized $ZrO_2$.

In some embodiments, the porous metal oxide catalyst comprises $Y_2O_3$. In some embodiments, the porous metal oxide catalyst is $Y_2O_3$.

In some embodiments, the catalyst composition improves product yield compared with a comparable reaction without the reactivating.

In some embodiments, the catalyst composition improves product yield at least 2-fold (such as, e.g., 2-fold, at least 5-fold, at least 10-fold, at least 25-fold, at least 50-fold, at least 75-fold, at least 100-fold, at least 125-fold, at least 150-fold, at least 175-fold) compared with a comparable reaction without the reactivating.

In some embodiments, the catalyst composition improves the rate of formation, the yield, or the selectivity of one or more desired products relative to the same reaction performed with the catalyst composition without the activating and/or reactivating.

Claims or descriptions that include "or" or "and/or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Furthermore, the disclosure encompasses all variations, combinations, and permutations in which at least one limitation, element, clause, and descriptive term from at least one of the listed claims is introduced into another claim. For example, any claim that is dependent on another claim can be modified to include at least one limitation found in any other claim that is dependent on the same base claim. Where elements are presented as lists, such as, e.g., in Markush group format, each subgroup of the elements is also disclosed, and any element(s) can be removed from the group. It should be understood that, in general, where the disclosure, or aspects of the disclosure, is/are referred to as comprising particular elements and/or features, embodiments of the disclosure or aspects of the disclosure consist, or consist essentially of, such elements and/or features. For purposes of simplicity, those embodiments have not been specifically set forth in haec verba herein. Where ranges are given (such as, e.g., from [X] to [Y]), endpoints (such as, e.g., [X] and [Y] in the phrase "from [X] to [Y]") are included unless otherwise indicated. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those of ordinary skill in the art will recognize or be able to ascertain using no more than routine experimentation, many equivalents to the specific embodiments of the disclosure described herein. Such equivalents are intended to be encompassed by the following claims.

EXAMPLES

The following examples are intended to be illustrative and are not meant in any way to limit the scope of the disclosure.

Example 1: DME Treatment on Y-Stabilized $ZrO_2$ $Y(NO_3)_3$ and $ZrOCl_2$ of target molar ratio were first dissolved in ethanol-water solution (1:4 ethanol-to-water volume ratio). Ammonium hydroxide (25 wt %) solution were added dropwise into the above solution dropwise to precipitate at ambient temperature under vigorous stirring. The resulting solution was aged at ambient temperature for 6 hours, before it was washed with ammonium hydroxide (25 wt %) solution and dried at 343 K and calcined at 873 K.

Treatment of Y-stabilized $ZrO_2$ promotes propane dehydrogenation (PDH) activity. Specifically, after 3.6 ks He treatment on 200 mg Y-stabilized $ZrO_2$ at 723 K, PDH areal rates, measured at 14 kPa propane, 12 kPa $H_2$, and 723 K, were 1 μmol $m^{-2}$ $h^{-1}$ (4% Y molar fraction in Y—Zr, denoted as 4% Y—Zr) and 0.3 μmol $m^{-2}$ $h^{-1}$ (10% Y molar fraction in Y—Zr, denoted as 10% Y—Zr). Applying 1 kPa DME treatments on these catalysts (10 kPa Ar, balanced with He) led to about 30-fold and about 70-fold rate enhancement on the 4% and 10% Y—Zr, respectively, suggesting that the DME treatments can remove surface $H_2O/CO_2$ titrants from Y—Zr surfaces. At identical reaction conditions (i.e., 14 kPa propane, 12 kPa $H_2$, and 723 K), the rate enhancements on Y—Zr were less than those observed on $ZrO_2$ (~180 fold less), and the measured PDH areal rates on the most active catalyst, 4% Y—Zr, was more than an order of magnitude smaller than that measured on DME-treated $ZrO_2$.

Example 2: DME Treatment on $Y_2O_3$

DME treatment enables surface cleaning of other metal oxides in addition to $ZrO_2$ and Y-stabilized $ZrO_2$. Illustratively, the promotional effect of DME treatment was also measured on $Y_2O_3$ powder. 100 mg $Y_2O_3$ powder was initially treated in He for 3.6 ks at 723 K, before the propane dehydrogenation (PDH) rate measurement at 14 kPa propane, 12 kPa $H_2$, and 723 K. The measured PDH rate was 0.26 mmol $g^{-1}$ $h^{-1}$. After the initial rate measurement, the catalyst was subsequently exposed to He for 1.8 ks before treatment in 1 kPa DME (10 kPa Ar, balanced with He) for 1.8 ks. PDH rate per catalyst mass, measured on DME treated $Y_2O_3$ without any oxidative treatment, decreased to 0.01 mmol $g^{-1}$ $h^{-1}$. This decrease may result from a carbonaceous deposit, derived from PDH reaction, which causes deactivation that is more severe on $Y_2O_3$ than on $ZrO_2$. Thus, a direct DME treatment, without any oxidative treatment, cannot remove these carbonaceous deposits. In fact, the treatment may instead lead to the formation of additional carbonaceous deposit, which renders the PDH rate to decrease after the DME treatment.

The catalyst was then oxidized in 02 (4 kPa, balanced with He) for 3.6 ks and purged in He for 1.8 ks, before another DME treatment at identical conditions as the previous one. PDH rate measured with the combination of oxidative and DME treatment shows a >10 fold increase, as compared to the initial PDH activity measured after He treatment, to 2.92 mmol $g^{-1}$ $h^{-1}$. Accordingly, oxidation before DME treatment may convert carbonaceous deposits into $H_2O$ and $CO_2$ titrants, and the DME then serves as a surface cleaner and reacts with $H_2O$ and $CO_2$ to remove these titrants from the active sites on $Y_2O_3$ surface in a similar manner as observed on $ZrO_2$ surfaces.

Example 3: Other Treatments on $ZrO_2$ $ZrO_2$ materials were prepared using a hydrothermal protocol described previously in Zhang et al., *Nat. Comm.*, 9:1-10 (2018) and involves mixing $ZrO(NO_3)_2 \cdot x\,H_2O$ aqueous solutions (12.3 g in 30 mL deionized water) and urea (21.6 g in 30 mL deionized water) followed by subsequent hydrolysis of urea, and increase in pH and the crystallization of $ZrO_2$ powders (453 K, 20 h), which were dried in ambient air at 383 K overnight.

Further experiments were performed to evaluate the necessary qualities for a surface cleaning reagent by applying chemical treatments other than DME on $ZrO_2$ catalysts. Specifically, select ether (i.e., diethyl ether), alcohols (i.e., methanol and ethanol), alkenes (propylene), and esters (ethyl acetate) were analyzed as potential "surface cleaning" reagents that could react with $H_2O$ and/or $CO_2$ with known stoichiometric reactions, with their effectiveness assessed in removing air-derived surface titrants and hence in promoting PDH areal rate. Herein, the enhancement factor of a treatment molecule i, i.e., $\chi_i$, was defined as the initial PDH areal rate ratio between that measured after applying such treatment i, i.e., $r_{PDH,i}$, and that measured after an direct, inert He treatment, i.e., $r_{PDH,He}$ at 14 kPa propane, 12 kPa $H_2$, and 723 K. A $\chi_i$ value of above unity indicates rate promotions, whereas below unity indicates rate inhibitions. Table 2 summarizes the effectiveness of these treatments.

TABLE 2

Summary of Enhancement Factor of a Treatment Molecule i ($\chi_i$) at 14 kPa Propane, 12 kPa $H_2$, and 723K on $ZrO_2$ Catalysts

| Entry | Treatment (i) | Pressure (kPa) | Duration | Enhancement factor ($\chi_i$) |
|---|---|---|---|---|
| 1 | He | 100 | 3.6 | 1 (benchmark) |
| 2 | DME | 1 | 1.8 | 176 |
| 3 | Diethyl ether (DEE) | 10 | 1.8 | 0.29 |
| 4 | Methanol | 5 | 1.8 | 30 |
| 5 | Ethanol | 2 | 1.8 | 0.68 |
| 6 | Ethyl acetate | 2 | 1.8 | 0.11 |
| 7 | Propylene | 0.5 | 1.8 | 2 |

It is clear from Table 2 that some chemical treatments are more effective than others in removing surface titrants and promoting the PDH rate (i.e., $\chi_i>1$). However, some treatments decrease the PDH rate, suggesting site-blocking instead of intended site-liberation (i.e., $\chi_i<1$). More specifically, it is noticeable that DME, methanol, and propylene treatments promote PDH areal rate relative to an inert, He treatment at 723 K. DME and methanol are the only oxygenates that clean the surface, as C1 ether and C1 alcohol cannot undergo dehydration reactions to form water without going through the energy-demanding surface carbene type of intermediate (e.g., $Zr{=}CH_2$) and also cannot undergo oxidation in the absence of oxidant to form $CO_2$. Alkenes such as propylene can remove surface $H_2O/CO_2$ presumably by steam/dry reforming reactions, but alkenes can also undergo side reactions such as further dehydrogenation and/or polymerizations that lead to the formation of H-deficient carbonaceous deposits that titrate the active sites. The other reagents, although known to react with $H_2O$ and/or $CO_2$ via stoichiometric reactions, instead lead to rate inhibitions instead of rate promotions (i.e., Entries 3, 5, and 6, Table 2). Indeed, on-line mass spectrometry analyses show that DEE, ethanol, and ethyl acetate treatments lead to the formation of $H_2O$ (m/z of 17 and 18), $H_2O$, and $CO_2$ (m/z of 28 and 44), respectively.

Without wishing to be bound by theory and based on the above experimental evidence, a surface cleaning reagent for porous metal oxide catalysts may possess one or more of the following properties:

It must react with $H_2O/CO_2$ via stoichiometric reactions;

It cannot lead to the formation of known surface titrants of Lewis acid-base pair (e.g., $H_2O/CO_2$); and It must itself have a way of exiting the surface, without being the irreversible titrant itself or leaving behind surface debris that can irreversibly titrate the active site.

What is claimed is:

1. A method of activating and/or reactivating, via a surface cleaning reagent, a catalyst composition comprising a porous metal oxide ($MO_x$) catalyst, the method comprising pretreating the porous metal oxide ($MO_x$) catalyst with the surface cleaning reagent at a partial pressure of the surface cleaning reagent of up to 10 kPa, wherein:

the surface cleaning reagent possesses at least one of the following characteristics:

possesses reactivity with one or more bound species derived from $CO_2$ and/or $H_2O$ via a stoichiometric reaction;

does not lead to one or more reactions that form a surface titrant of a Lewis acid-base pair; and/or can desorb from a surface of the porous metal oxide catalyst without leaving behind surface debris that can irreversibly titrate an M-O active site of the porous metal oxide catalyst; and further wherein:

if the porous metal oxide catalyst is $ZrO_2$, then the surface cleaning reagent is not dimethyl ether or propylene.

2. A method of activating and/or reactivating, via a surface cleaning reagent, a catalyst composition comprising a porous metal oxide ($MO_x$) catalyst, the method comprising pretreating the porous metal oxide ($MO_x$) catalyst with the surface cleaning reagent at a partial pressure of the surface cleaning reagent of up to 10 kPa, wherein:

the surface cleaning reagent is chosen from alcohols, ketones, carboxylates, acids, esters, ethers, hemiacetals, hemiketals, acetals, ketals, orthoesters, orthocarbonates, organic acid anhydrides, and combinations thereof; and further wherein:

if the porous metal oxide catalyst is $ZrO_2$, then the surface cleaning reagent is not dimethyl ether or propylene.

3. A method of activating and/or reactivating, via a surface cleaning reagent, a catalyst composition comprising a porous metal oxide ($MO_x$) catalyst, the method comprising pretreating the porous metal oxide ($MO_x$) catalyst with the surface cleaning reagent at a partial pressure of the surface cleaning reagent, the pretreating performed at a temperature between 323 K and 900 K, wherein:

the surface cleaning reagent comprises at least one compound chosen from ROH, RCOR', RCHO, ROCOOR', RCOOH, RCOOR', $R_2CH(OR_1)(OH)$, RC(OR")(OH)R', RCH(OR')(OR"), RC(OR")(OR") R', RC(OR')(OR")(OR"), C(OR)(OR')(OR")(OR"), and $R_1(CO)O(CO)R_2$, wherein each of R, R', R", R", $R_1$, and $R_2$ is independently chosen from alkyl, alkenyl, alkynyl, and aryl groups;

and further wherein:

if the porous metal oxide catalyst is $ZrO_2$, then the surface cleaning reagent is not dimethyl ether or propylene.

4. The method according to claim 3, wherein R, R', R", R", $R_1$, and $R_2$ do not possess a —$CH_2CH_3$ pendant group, and R, R', R", R", $R_1$, and $R_2$ do not possess a —$CH_2CH_3$ terminal group.

5. The method according to claim 1, wherein the surface cleaning reagent possesses reactivity with one or more bound species derived from $H_2O$ via a stoichiometric reaction.

6. The method according to claim 1, wherein a metal (M) of the porous metal oxide catalyst does not undergo reduction to a lower oxidation state in a reductive environment typical of hydrogenation-dehydrogenation catalysis.

7. The method according to claim 1, wherein the porous metal oxide catalyst comprises at least one of $ZrO_2$, $Y_2O_3$, $CeO_2$, and CoO.

8. The method according to claim 1, wherein the porous metal oxide catalyst is chosen from oxides of Y, Ce, and Ti, and mixed oxides thereof.

9. The method according to claim 1, wherein the porous metal oxide catalyst comprises one or more of Y, Nb, B, Ga, Co, and Mo on $ZrO_2$.

10. The method according to claim 1, wherein:

the porous metal oxide catalyst comprises one or more of Mg, Ca, Sr, Ba and La on a zirconia support; or the porous metal oxide catalyst comprises $ZrO_2$-silica, zirconia-alumina, zirconia-titania, or a combination thereof.

11. The method according to claim 1, wherein the porous metal oxide catalyst comprises $ZrO_2$, Y-stabilized $ZrO_2$, or $Y_2O_3$.

12. The method according to claim 1, wherein the surface cleaning reagent is chosen from dimethyl ether, propylene, methanol, tert-butyl alcohol, methyl tert-butyl ether, di-tert-butyl ether, anisole, dimethyl carbonate, and combinations thereof.

13. The method according to claim 1, wherein the pretreating is performed at a temperature between 323 K and 900 K.

14. The method according to claim 1, further comprising pretreating the catalyst composition in an aerobic oxidative environment before or after the pretreatment with the surface cleaning reagent.

15. A method of catalyzing a reaction on a catalyst composition comprising a porous metal oxide catalyst, the method comprising activating and/or reactivating the catalyst composition using the method of claim 1, wherein the reaction is chosen from alkane dehydrogenation, alkene hydrogenation, olefin-paraffin alkylation, methanol synthesis from $CO/H_2$ mixtures without O-rejection as $H_2O$ or $CO_2$, C—C bond formation via alkene oligomerization or metathesis, dehydrocyclization (alkanes/alkenes to arenes), dehydrocyclodimerization (alkanes/alkenes to arenes with a larger number of C-atoms), transfer hydrogenation, hydroformylation/carbonylation, aromatization, dearomatization, reforming, isomerization, and bifunctional reactions in which one of the aforementioned functions can be combined with a Brønsted acid function.

16. The method according to claim 15, wherein the bifunctional reaction is chosen from catalytic reforming for octane enhancement, alkane hydroisomerization, hydrocracking, isodewaxing, fluid catalytic cracking, and reactions converting $C_3$-C4 alkanes to aromatics.

17. The method according to claim 15, wherein the reaction is propane dehydrogenation.

18. The method according to claim 15, wherein the porous metal oxide catalyst comprises at least one of $ZrO_2$, $Y_2O_3$, $CeO_2$, and CoO.

19. The method according to claim 15, wherein the porous metal oxide catalyst comprises $ZrO_2$.

20. The method according to claim 15, wherein the porous metal oxide catalyst comprises Y-stabilized $ZrO_2$.

* * * * *